United States Patent
Mickel et al.

[11] Patent Number: 6,062,575
[45] Date of Patent: *May 16, 2000

[54] TOOL SHAFT COUPLER

[75] Inventors: Thomas J. Mickel, Jupiter; Stewart W. Willason, Palm Beach Gardens, both of Fla.

[73] Assignee: Mednext, Inc., West Palm Beach, Fla.

[*] Notice: This patent is subject to a terminal disclaimer.

[21] Appl. No.: 09/068,370

[22] PCT Filed: Dec. 1, 1995

[86] PCT No.: PCT/US95/15723
§ 371 Date: May 7, 1998
§ 102(e) Date: May 7, 1998

[87] PCT Pub. No.: WO97/20653
PCT Pub. Date: Jun. 12, 1997

Related U.S. Application Data

[63] Continuation-in-part of application No. 08/281,489, Jul. 27, 1994, Pat. No. 5,490,683.

[51] Int. Cl.[7] .................................................. B23B 31/107
[52] U.S. Cl. .............................. 279/75; 433/128; 606/79; 408/226; 408/239 R
[58] Field of Search .................................. 279/74, 75, 82, 279/125; 403/322, 325; 408/239 R, 239 A, 240, 226, 710; 433/128; 606/79, 80

[56] References Cited

U.S. PATENT DOCUMENTS

| | | | |
|---|---|---|---|
| 2,807,473 | 9/1957 | Kiehne | 279/75 |
| 5,490,683 | 2/1996 | Mickel et al. | 279/75 |
| 5,569,256 | 10/1996 | Vaughn et al. | 279/75 |
| 5,741,263 | 4/1998 | Umber et al. | 279/75 |

*Primary Examiner*—Steven C. Bishop
*Attorney, Agent, or Firm*—Woodard, Emhardt, Naughton Moriarty & McNett

[57] ABSTRACT

Apparatus and methods for coupling a driving shaft (60) and a mating tool shaft (50, 50') to transmit rotational forces and axial tension and compression between the shafts. The coupler (15) provides for axial tension transmission through tension transmission surfaces (80, 80') spaced-apart from torque (54, 54') and compression (55, 55') transmission surfaces of the mating tool shaft (50, 50'). A separate safety lock release attachment (17) is preferably removed during tool shaft rotation and can automatically hold the driving shaft (60) stopped when used to release the shaft locking means for a tool change. An optional reversible mechanical interlock (91, 92) further ensures that the driving shaft (60) will remain stopped during a tool change. Malfunction (e.g., improper seating) of the shaft locking means with the attachment ring (70) in place results in a positive visual indication of the malfunction.

39 Claims, 5 Drawing Sheets

TOOL SHAFT COUPLER

This application is a continuation-in-part of application Ser. No. 08/281,489, filed Jul. 27, 1994, which issued as U.S. Pat. No. 5,490,683.

FIELD OF THE INVENTION

The invention relates to methods and apparatus for reversibly coupling rotating shafts.

COUPLING TOOLS TO HIGH-SPEED MOTORS

Many types of rotary tools are preferably coupled to a driving shaft with a safe and reliable coupler which is also reversible (allowing for the rapid removal of a tool from the coupling and/or the coupling of one tool in place of another to a driving shaft). Applications in which there are particularly stringent safety and reliability requirements for couplers include the drilling, grinding, polishing and related material-removal operations which are inherent in many medical and dental treatment plans. Rotary tools (e.g., drills, burs, grinding wheels and cutting wheels) reversibly coupled to high-speed motors can precisely shape tooth, bone, or biocompatible implant material during certain surgical procedures. Such shaping operations often require precise tool positioning and as many as thirty tool changes in the course of a single operation. Thus, each rotating tool shaft would preferably be lockable securely into its coupler (i.e., substantially preventing its accidental disconnection from the coupler), but the lock would preferably be easily and surely reversed to allow tool insertion or removal or tool changes.

Surgical applications of a tool shaft coupler include a requirement to keep the total time under anesthesia as short as possible for each patient. Thus, connecting and disconnecting tools via a reversibly locking tool shaft coupler should preferably be quick and simple, even for a person wearing surgical gloves. Required motions to lock or unlock the connector, or to insert or remove a tool should be relatively uncomplicated. Further, because tools may reach rotational speeds in excess of 20,000 revolutions per minute, positive (and separate) indications would preferably be provided to clearly signify to a human operator either improper placement of a tool shaft within a coupler or inoperability of a coupler shaft lock. Moreover, once connected, a tool shaft and tool shaft coupler should not be subject to accidental unlocking (which could allow disconnection of the tool), either due to operator error or mechanical failure. Thus, a tool shaft coupler lock release mechanism would preferably comprise a separate coupler unlocking component which would be required to release the lock but which would normally be removed before the motor applies torque to the tool. Accidental failure of the operator to remove the unlocking component should not, however, pose a safety hazard during relatively brief operation of the motor. Further, accidental application of motor power to a tool shaft coupler during changing of a tool should not result in driving shaft rotation before the tool is securely locked in the coupler.

Tool shaft couplers should be capable of transmitting axial forces (i.e., tension or compression forces acting substantially parallel to the tool shaft longitudinal axis) alone or in combination with torque (i.e., rotational forces acting substantially about the tool shaft longitudinal axis). All such forces should be effectively transmitted, i.e., without substantial axial displacement of the tool shaft with respect to the driving shaft, without substantial rotational slippage of the driving shaft with respect to the tool shaft, and without substantial distortion of the driving shaft, tool shaft or coupler. Any tool shaft coupling failure leading to shaft displacement, deformation, distortion or slippage could lead to whipping of the tool shaft, increased vibration, tool overheating and/or tool shaft breakage. In turn, any of these events could lead to accidental uncoupling of the tool shaft from the driving shaft, leading to a risk of patient injury and possible difficulty in removing a damaged tool shaft from a coupler. These problems would be particularly acute in coupler and tool designs wherein both torque and axial forces are transmitted by substantially identical tool shaft surfaces. Hence, improved tool shaft couplers and mating tool shafts would comprise surfaces used to transmit torque which would preferably be different from those used to transmit axial forces. Even more preferably, at least some surfaces transmitting torque and axial forces would preferably be spaced apart to avoid or reduce potentially damaging stress concentrations within a tool shaft and/or driving shaft.

Additional sources of stress in tool and driving shafts or couplers are various vibration modes due, for example, to unbalance in couplers, tools and/or tool shafts. Vibration can also be induced by distortion of the shafts and nonconcentricity of driving shafts, tool shafts and/or coupler components due to lateral and/or angular misalignment.

SUMMARY OF THE INVENTION

The invention comprises reversibly locking tool shaft couplers and mating tool shafts, and methods of using the couplers to drivingly couple a driving shaft and a mating tool shaft drivingly (effectively) engaged therewith. The couplers and mating tool shafts incorporate design improvements to enhance safety and ease of operation, and comprise surfaces and/or structures for drivingly coupling (i.e., for transmitting torque and axial forces between) a driving shaft and a mating tool shaft. Note that a driving shaft to which a tool shaft coupler of the present invention could be applied would be a driving shaft (substantially rigid or flexible) which is rotatable about a substantially longitudinal axis within a driving shaft housing. Note also that a mating tool shaft may comprise a portion of a tool itself (e.g., the shank of a drill bit or burr), or a shaft which itself is drivingly coupled with a tool shaft (e.g., a flexible or geared shaft tipped with a tool or coupled to a tool shaft).

A tool shaft coupler of the present invention comprises at least one torque transmission surface fixedly coupled to the driving shaft for axially slidingly mating with a mating tool shaft to transmit torque between the mating tool shaft and the driving shaft. Additionally, the coupler comprises at least one compression transmission surface as well as tension transmission means, the tension transmission means being spaced apart from the at least one compression transmission surface and the at least one torque transmission surface, and comprising at least one tension transmission surface and at least one movable tension-resisting member, the at least one tension-resisting member being reversibly and slidingly movable to a tension-resisting position to couple the driving shaft and a mating tool shaft to reversibly limit maximum axial movement of the mating tool shaft with respect to the driving shaft under an axial tension load (i.e., a force substantially parallel to the tool shaft longitudinal axis which tends to pull the driving and mating tool shafts apart).

The at least one compression transmission surface is fixedly coupled to the driving shaft for substantially limiting maximum axial movement of a mating tool shaft with respect to the driving shaft under an axial compression load.

For reversibly locking said at least one tension-resisting member in a tension-resisting position, the invention comprises shaft locking means having an (optionally high-friction and/or mechanically engaging) engagement surface (for slidably engaging safety lock release means), the shaft locking means being slidably coupled to the driving shaft. The slidable coupling of the shaft locking means to the drive shaft may also include guide means which act to substantially prevent rotation of the shaft locking means with respect to the drive shaft while allowing substantially free sliding coupling as described herein.

Preferred embodiments of tool shaft couplers of the present invention may also comprise substantially toroidal safety lock release means and attachment means, the attachment means being reversibly coupled (e.g., as by screw threads or a twist-lock connector) to the driving shaft housing and serving one or more functions, as in guiding a mating tool shaft during connection to or disconnection from a coupler, supporting the tool shaft with one or more bearings, facilitating locking and/or unlocking of a coupler, and/or reducing any likelihood of tool shaft whipping (i.e., tool shaft rotation which is not substantially confined to rotation about the tool shaft longitudinal axis). The attachment means comprise at least one spindle cap access slot and may interact with the substantially toroidal safety lock release means which are slidably positionable over said attachment means and slidingly engagable through said at least one spindle cap access slot with said engagement surface of said shaft locking means to move said shaft locking means to a first unlocking position for allowing said at least one tension-resisting member to move from said tension-resisting position to allow reversible placement of a mating tool shaft within said shaft locking means, and to allow movement of said shaft locking means to a second locking position for moving said at least one tension-resisting member to said tension-resisting position and for reversibly locking said at least one tension-resisting member in said tension-resisting position. Safety lock release means may alternatively comprise (in addition to or in place of the substantially toroidal safety lock release means) a lock release lever reversibly insertable in one or more lever access ports in the attachment means and movable therein to facilitate unlocking of a coupler.

Besides the tool shaft coupler described herein, the present invention may additionally comprise one or more other improvements, including a mating tool shaft with correspondingly shaped and positioned axial force and torque transmission surfaces, as well as a method of coupling a driving tool shaft and a mating tool shaft, and warning means to visually indicate improper seating of a mating tool shaft in the coupler and/or malfunction of said shaft locking means. The warning means preferably comprise at least a warning portion of the attachment means and/or the mating tool shaft, each warning portion having a distinctive visual appearance and being visible to a user in case of malfunction of the shaft locking means and/or to indicate improper seating of a mating tool shaft in the coupler respectively.

In preferred embodiments of mating tool shafts, one or more warning bands of distinctive visual appearance may be applied to the portion of a mating tool shaft surface adjacent to and just concealed by the attachment means when the mating tool shaft is drivingly engaged with the tool shaft coupler. Because such driving (effective) engagement implies sliding insertion of the mating tool shaft within the coupler to an effective depth wherein all corresponding axial force and torque transmission surfaces on the mating tool shaft and in the coupler are substantially fully engaged, faulty engagement of the force transmission surfaces occurs when the mating tool shaft is inserted in the coupler to a depth less than the effective depth. Insertion of a mating tool shaft to a less-than-effective depth (that is, the mating tool shaft is not drivingly coupled to the tool shaft coupler) will then preferably leave visible at least part of a visually distinct proximal portion on the mating tool shaft which is unconcealed by the attachment means, thus providing a visual warning of the tool shaft's improper insertion into the coupler. This visually distinct proximal portion of the mating tool shaft would, of course, not be visible outside of the attachment means when the tool shaft is drivingly coupled to the tool shaft coupler. For embodiments comprising the toroidal safety lock release means, a visually distinctive warning portion of the attachment means would be substantially visible with the toroidal safety lock release means contacting the shaft locking means in the first (unlocking) position, and substantially invisible with the toroidal safety lock release means contacting the shaft locking means in said second (locking) position.

DETAILED DESCRIPTION

In the following description, two alternative embodiments of the mating tool shaft 50,50' are identified, the embodiments being substantially similar except for differing forms of tension transmission surface 53,53'. Only one embodiment (i.e., either 50 or 50') of a mating tool shaft is used with tool shaft coupler 15 at any one time. Since in general one or the other of the embodiments 50 and 50' may be desired in certain applications, both embodiments are identified when a general reference to a mating tool shaft is required in the following discussion. Other corresponding features of mating tool shaft 50,50' are similarly identified by unprimed and primed numbers respectively.

Referring to FIGS. 1A, 1B, 3A, 3B, 3C, 4, 4A and 5 for schematic illustrations of the features discussed, a preferred embodiment of the invention is seen to comprise a tool shaft coupler 15 for drivingly coupling a driving shaft 60 with a mating tool shaft 50,50' which is effectively engaged with the driving shaft 60, the driving shaft 60 being rotatable about a substantially longitudinal axis BB within a driving shaft housing 65 (which in turn is fixedly coupled to driving shaft housing end piece 65'). Note that for the sake of clarity in the schematic illustrations, components and features described herein may be labeled only in the figure(s) in which they appear most clearly.

A mating tool shaft 50,50' has surfaces and/or structures functionally and spatially corresponding to surfaces and/or structures within tool shaft coupler 15. Effective engagement of a mating tool shaft 50,50' comprises insertion of mating tool shaft 50,50' within the tool shaft coupler 15 an effective distance which would allow substantially full mating of corresponding torque and axial force transmission surfaces and effective engagement of the mating tool shaft 50,50' with the shaft locking means. With the corresponding torque and axial force (i.e., compression and tension) transmission surfaces, or structures comprising one or more of such surfaces of the tool shaft coupler 15 and the mating tool shaft 50,50' thus brought into effective apposition, transmission of torque and axial compression and tension forces between the driving and mating tool shafts may then take place. However, effective engagement of a mating tool shaft 50,50' with respect to the driving shaft 60 also facilitates reversible locking of a mating tool shaft 50,50' within the tool shaft coupler 15. Such locking in the present invention includes an optional safety feature wherein malfunction of which will be readily apparent to a human operator of the tool through the appearance of one or more areas of distinctive visual appearance on attachment means 17 and/or mating tool shaft 50,50'.

Surfaces for transmission of torque and axial forces within a tool shaft coupler 15 are preferably fixedly coupled (attached) to (e.g., as by welding, brazing, crimping, swaging, screwing, clamping, or by interference fit), or by forming as an integral part of a driving shaft 60 which, in preferred embodiments, comprises a motor shaft or a shaft which is drivingly coupled to a motor shaft (as by a flexible shaft in certain embodiments). Typically, a driving shaft 60 will be rotatable within a driving shaft housing 65, the housing 65 (e.g., a motor stator) often providing a convenient hand grip for a human operator. Surfaces for transmission to the driving shaft 60 of (axial) tension on the mating tool shaft 50,50' (tending to pull the mating tool shaft 50,50' away from the tool shaft coupler 15 substantially along longitudinal axis BB) are spaced apart from the surfaces for transmission of torque and (axial) compression forces.

Tool shaft coupler 15 comprises at least one torque transmission surface (see, e.g., surface 64 of spindle chip 62 in FIG. 3A) fixedly coupled to the driving shaft 60 for axially slidingly mating with a corresponding torque transmission surface 54,54' of mating tool shaft 50,50' to transmit torque between mating tool shaft 50,50' and the driving shaft 60. Note that torque transmission surface 64 may, for example, be formed as an inherent part of driving shaft 60 or, as in FIGS. 1A, 1B, 3A, 3B, 3C and 4, torque transmission surface 64 may be formed on a separate piece of material (e.g., spindle chip 62) which is then itself fixedly attached to driving shaft 60. The latter configuration may be preferable in certain applications because it allows spindle chip 62 to be fabricated and hardened separately from driving shaft 60. Note also that the configuration shown in cross section in FIG. 3C (i.e., wherein a torque transmission surface lies substantially in a single plane and has a width substantially equal to the diameter of spindle chip 62) may be replaced by other preferred configurations having a plurality of torque transmission surfaces lying in two or more different planes (e.g., as in a square or hexagonal drive). However, for certain relatively high-torque applications, the configuration illustrated in FIGS. 3A, 3B and 3C may be preferred because it provides substantial torque transmission capability with a relatively low likelihood of distortion (e.g., rounding of corners) on spindle chip 62 or mating tool shaft 50,50'.

Tool shaft coupler 15 also comprises tension transmission means spaced apart from said at least one torque transmission surface and comprising at least one tension transmission surface (e.g., the walls 80,80' of substantially cylindrical holes in which balls 82,82' respectively substantially reside as schematically illustrated) and at least one movable tension-resisting member (e.g., balls 82,82' comprising hardened steel or, preferably, chrome alloy steel). Note that although two tension-resisting members (i.e., balls 82,82') and two tension transmission surfaces (i.e., the walls 80,80' of substantially cylindrical holes) are illustrated herein, one ball or more than two balls in their respective substantially cylindrical holes, spaced (preferably substantially evenly) around the circumference of driving shaft 60, may be preferred for certain relatively high-load applications. Note further that although the illustrated embodiments of tool shaft coupler 15 comprise equal numbers of tension-resisting members and tension transmission surfaces, the number of tension-resisting members may exceed the number of tension transmission surfaces in cases where two or more tension-resisting members simultaneously engage a single tension transmission surface (e.g., two or more tension-resisting members are present substantially side-by-side in an elongated hole).

Figure 3A:
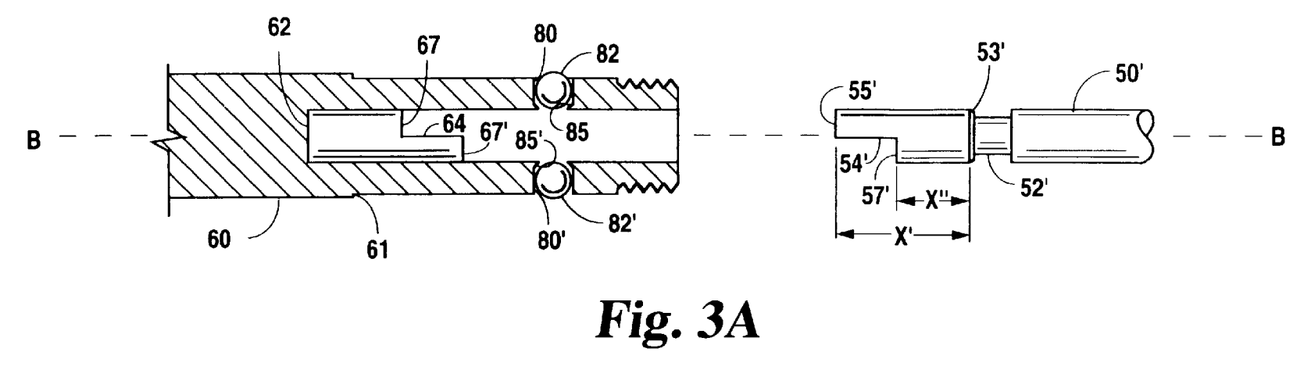
FIG. 3A schematically illustrates (in partial cross-section) a disconnected view of a driving shaft and mating tool shaft, including tension-resisting members.

As illustrated, balls 82,82' are substantially free to move substantially radially within substantially cylindrical walls 80,80' respectively, except as limited by the inner surface 75 (the inner surface 75 itself comprising a cam surface 72) of spindle cap 70 (which limits movement of balls 82,82' away from driving shaft 60), and by retaining ledges 85,85' (seen best in FIG. 3A) which limit movement of balls 82,82' respectively toward the longitudinal axis BB. Ledges 85,85' preferably comprise substantially frusto-conically shaped surfaces which neck-down or reduce the nominal inner diameter of substantially cylindrical walls 80,80'. Ledges 85,85' thus limit the movement of balls 82,82' respectively toward axis BB when a mating tool shaft 50,50' is not present within driving shaft 60 (as shown in FIG. 3A). The portion of a mating tool shaft 50,50' (other than any tension transmission surface) which is proximate ledges 85,85' when the tool shaft 50,50' is drivingly engaged in a coupler 15 is intentionally spaced apart from spindle cap 70 and other portions of the shaft locking means. Thus if balls 82,82' that contact spindle cap 70 are not simultaneously in contact with a tension transmission surface, then they can not be in contact simultaneously with tool shaft 50,50' in any manner. This spacing prevents balls 82,82' (or other analogously sized tension-resisting members) from exerting purely lateral force on tool shaft 50,50' during normal operation, and thus tends to reduce tool shaft vibration in cases where tool shaft 50,50' is not exactly coaxial with driving shaft 60. In combination with the lateral clearance provided between tool shaft 50,50' and driving shaft 60, the function of tension-resisting members in the present invention approximates a (laterally and longitudinally) compliant universal joint for tool shaft 50,50' which allows the shaft to "float" to a limited extent while still restrained, the (lateral and/or longitudinal) floating action acting to reduce transmission of vibration from the tool shaft 50,50' to the driving shaft 60 (and thence to the hand of the operator in certain preferred embodiments).

Figure 4:
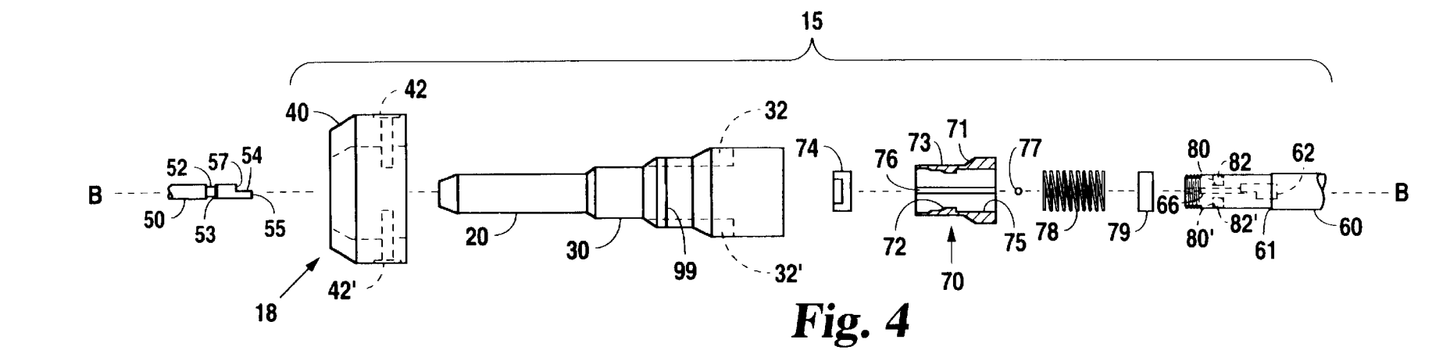
FIG. 4 schematically illustrates (in partial cross-section) an exploded view of a tool shaft coupler, including attachment means and toroidal safety lock release means.
Figures 4A, 5:
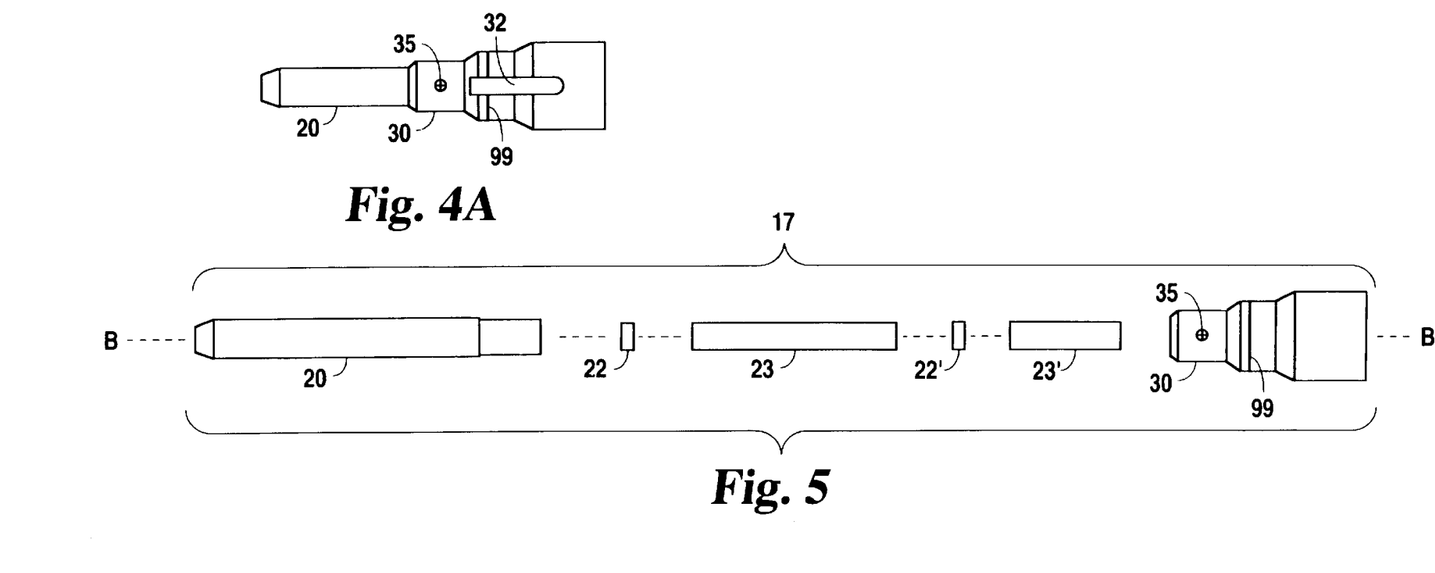
FIG. 4A schematically illustrates tool shaft coupler attachment means rotated 90 degrees relative to the attachment means view in FIG. 4.
FIG. 5 schematically illustrates an exploded view of tool shaft coupler attachment means.

Tool shaft 50,50' is preferably substantially oriented with respect to driving shaft 60 by one or more bearings (distal and proximal journal bearings 22,22' respectively are schematically illustrated in FIG. 5) within attachment means 17. Substantially coaxial tool shaft orientation as above by one or more bearings 22,22' of attachment means 17 may include errors due to lateral displacement and/or angular displacement with respect to driving shaft 60. The above spacing conditions regarding tension-resisting members are beneficial in reducing adverse effects (e.g., vibration and wear) due to possible orientation error(s).

Figure 1A:
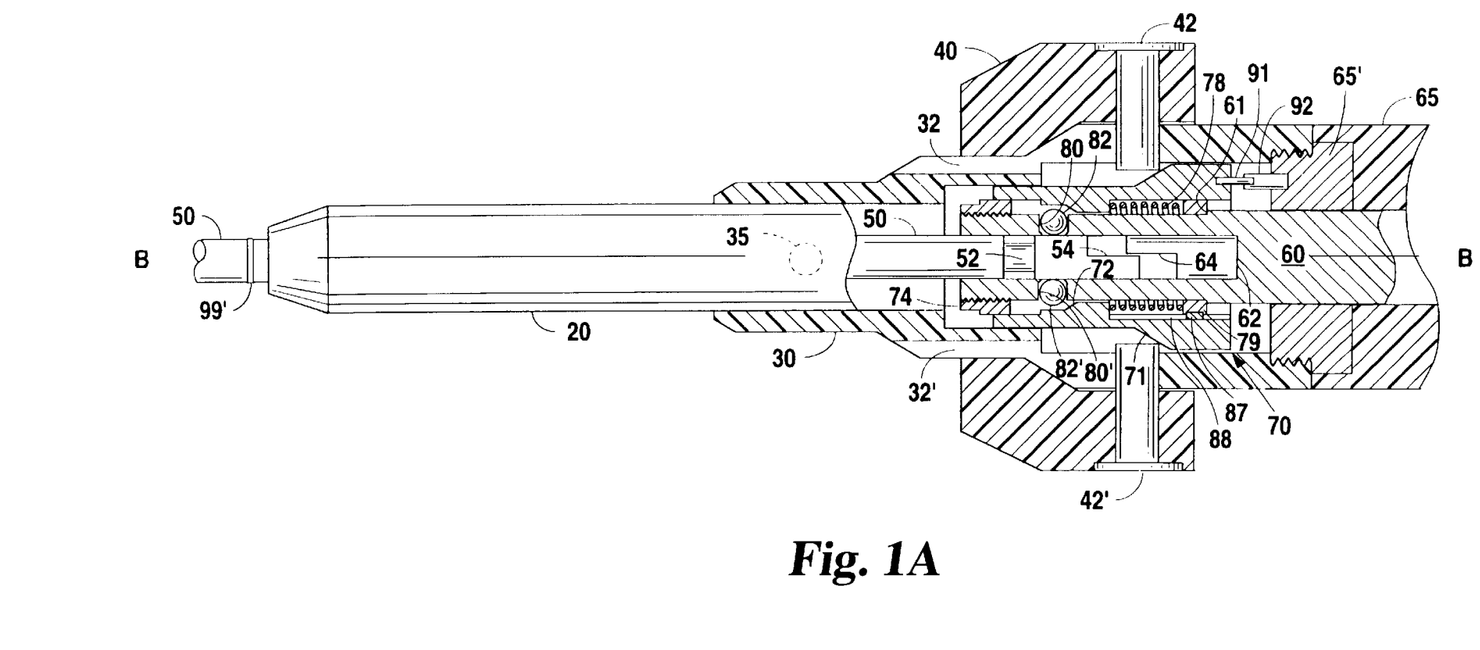
FIG. 1A schematically illustrates a preferred embodiment of a tool shaft coupler including attachment means and toroidal safety lock release means in a first, unlocking, position (in partial cross-section).
Figure 1B:
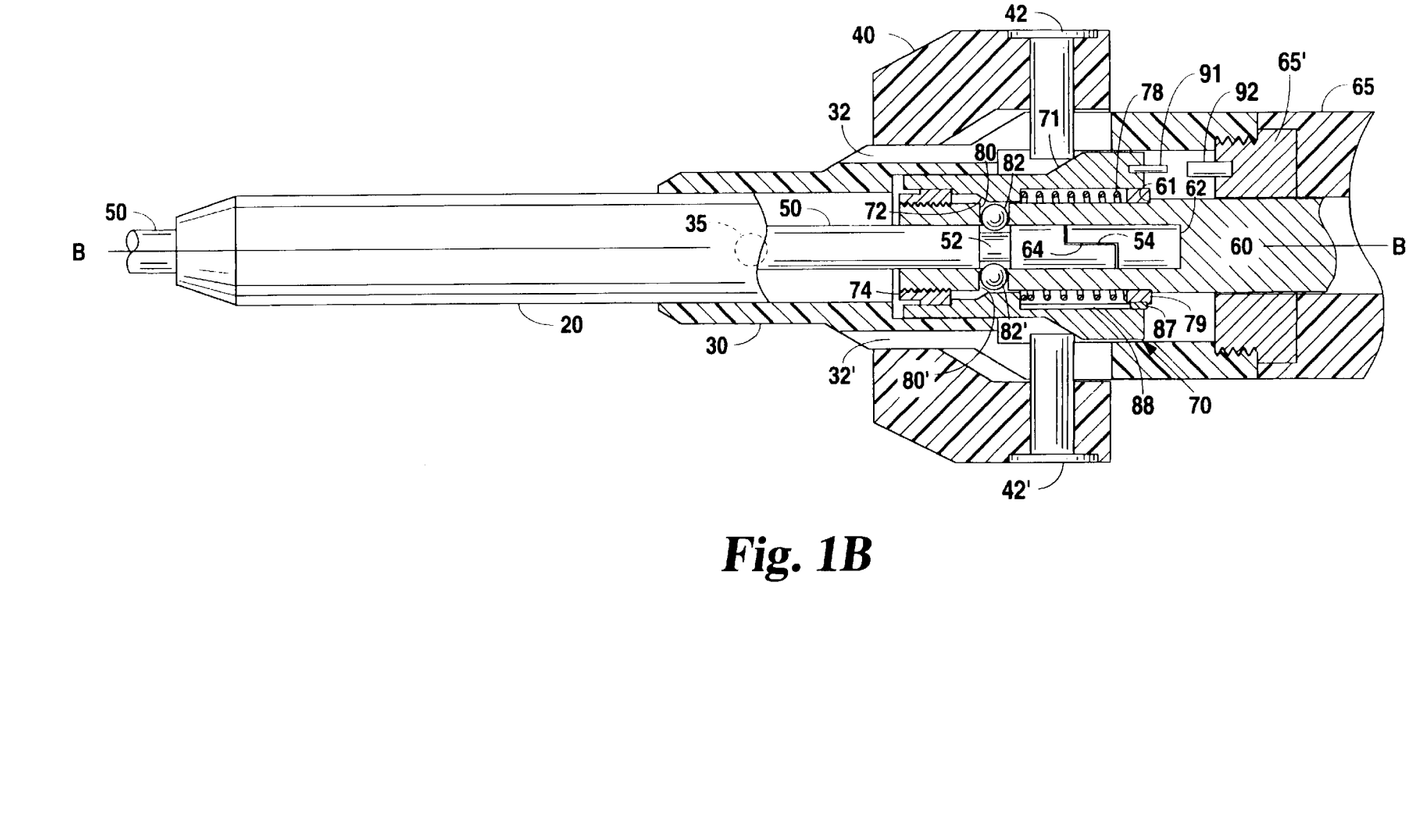
FIG. 1B schematically illustrates a preferred embodiment of a tool shaft coupler including attachment means and toroidal safety lock release means in a second, locking, position (in partial cross-section).
Figure 3B:
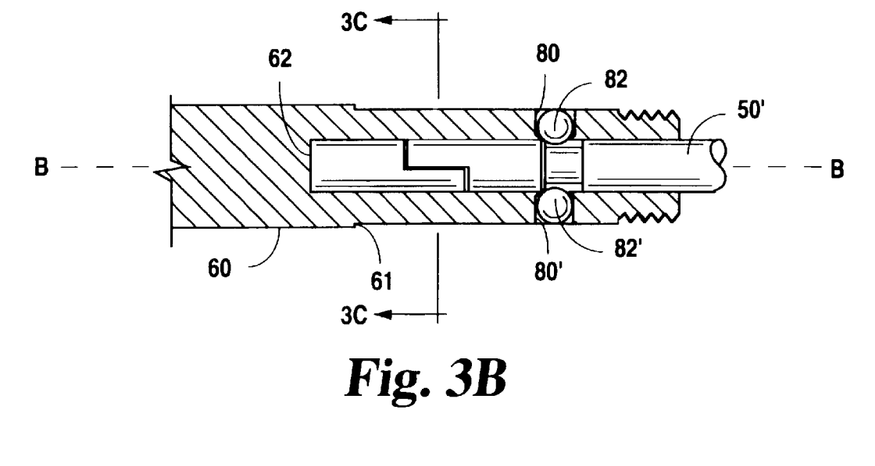
FIG. 3B schematically illustrates (in partial cross-section) a connected view of a driving shaft and mating tool shaft, including tension-resisting members.

But for effective retention when a mating tool shaft 50,50' is inserted within driving shaft 60 so as to effectively engage torque transmission surface 64 (as shown in FIGS. 1B and 3B), ledges 85,85' do allow balls 82,82' respectively to move into a tension-resisting position, which would allow substantially simultaneous (interference) contact of balls 82,82' with both substantially cylindrical walls 80,80' respectively and tension transmission surface 53,53' of mating tool shaft 50,50'. If the balls 82,82' are held in such a tension-resisting position (e.g., by the inner surface 75 of spindle cap 70, as shown in FIG. 1B), mating tool shaft 50,50' could not be disconnected (i.e., withdrawn) from effective engagement with torque transmission surface 64 by a tension force tending to separate driving shaft 60 and mating tool shaft 50,50' which is applied substantially parallel to longitudinal axis BB. Such a tension force would put balls 82,82' in compression because of the interference nature of such a tension-resisting position. Note that the groove 52,52', one portion of which is tension transmission surface 53,53', is preferably deep enough so that balls 82,82' never touch the groove surface closest to axis BB (i.e., balls 82,82' preferably can not bottom out in groove 52,52').

Note also that balls 82,82' are shown in similar tension-resisting positions in FIG. 1B and in FIG. 3B, but with mating tool shafts 50 and 50' in the two figures respectively. The difference between mating tool shafts 50 and 50', which is schematically illustrated in FIGS. 1B and 3B respectively, is that mating tool shaft 50 comprises groove 52 and tension transmission surface 53 (see FIG. 4), whereas mating tool shaft 50' comprises groove 52' and tension transmission surface 53'. Surface 53, as illustrated in FIG. 4, lies substantially entirely in a plane which is itself substantially perpendicular to longitudinal axis BB. Thus, contact of balls 82,82' with surface 53 is substantially limited to its outer (substantially circular) peripheral edge.

In contrast, tension transmission surface 53' is a substantially frusto-conically shaped surface which is substantially symmetrical about longitudinal axis BB, surface 53' being oriented to allow balls 82,82', when in tension-resisting positions, to contact portions of surface 53' which are closer to longitudinal axis BB than the outer (substantially circular) periphery of the surface 53'. Tension transmission by surface interference contact between balls 82,82' and surface 53' may better limit axial free play between driving and mating tool shafts (compared to interference contact between balls 82,82' and the outer edge of surface 53) in certain applications having relatively high axial tension loads tending to separate a tool shaft from tool shaft coupler 15. Assuming a substantially fixed distance between an interference tension-resisting position of a tension-resisting member (e.g., one of the balls 82,82') and the compression transmission surface 67 (see FIG. 3A) of a tool shaft coupler 15, axial free play then becomes substantially a function of the distance between compression transmission surface 67 and tension transmission surface 53 or 53' on a mating tool shaft 50 or 50' respectively (the latter measurement is labeled X' on FIG. 3A). In certain applications, surface 53' is more protected (and thus less subject to wear) than the peripheral edge of surface 53. Edge wear on surface 53, when combined with normal manufacturing tolerances, may then result in unacceptably large values of possible relative motion (free play) between driving shaft 60 and mating tool shaft 50, substantially along longitudinal axis BB, even when balls 82,82' are very repeatably moved into tension-resisting positions.

The said at least one tension-resisting member (e.g., balls 82,82' for illustrative purposes) is reversibly and slidingly movable through the action of the inner spindle cap surface 75, which in turn comprises a cam surface 72. Spindle cap 70 is springingly coupled to driving shaft 60 through the action of spring 78 acting on spring stop ring 79. Spring stop ring 79 in turn rests against driving shaft shoulder 61 to transfer the force of spring 78 to driving shaft 60. Spindle cap 70 is retained on driving shaft 60 by spindle cap nut 74.

Thus, if spindle cap 70 is first moved to compress spring 78 (i.e., moved toward the right as in FIG. 1A to a first or unlocking position), a mating tool shaft 50,50' may, if present within coupler 15, be substantially freely withdrawn from coupler 15. If, on the other hand, a mating tool shaft 50,50' is not effectively engaged in coupler 15 when spindle cap 70 is moved to a first (unlocking) position, a mating tool shaft 50,50' may then be inserted and effectively engaged with torque transmission surface 64. Spindle cap 70 may then be released to move to the left toward its resting position with spring 78 extending and cam surface 72 contacting balls 82,82' (as in FIG. 1B). As cam surface 72 contacts both balls 82,82', the balls are substantially simultaneously moved by cam surface 72 into tension-resisting positions (assuming a mating tool shaft 50 or 50' is at that time inserted sufficiently far into coupler 15 to effectively engage with torque transmission surface 64). When cam surface 72 has maximally moved balls 82,82' into tension-resisting positions, continued movement of spindle cap 70 in a direction which would tend to extend spring 78 is effectively stopped by spindle cap nut 74. The interference tension-resisting positions of balls 82,82' thus act to couple the driving shaft 60 and a mating tool shaft 50 (or 50') to reversibly limit (in conjunction with compression transmission surfaces 55 or 55' and 67) maximum axial movement (i.e., movement substantially parallel to longitudinal axis BB) of the mating tool shaft 50,50' with resect to the driving shaft 60 under alternating axial compression and tension loads. Such maximum axial movement is preferably less than about 0.020 inches to improve mating tool shaft placement precision, more preferably less than about 0.010 inches to reduce the risk of shaft vibration and most preferably less than about 0.005 inches to reduce wear on components of tool shaft coupler 15. Note that alternate compression transmission surfaces 57 or 57' and 67' may act in an analogous manner to that described above for compression transmission surfaces 55 or 55' and 67 to reversibly limit maximum axial movement of a mating tool shaft 50,50'. When so acting, compression transmission surface 57 or 57' is preferably spaced apart from the corresponding tension transmission surface (53 or 53' respectively) by a distance (indicated by X" in FIG. 3A) which will limit maximum axial tool shaft movement in the manner described above.

All embodiments of tool shaft couplers 15 of the present invention comprise at least one compression transmission surface (see, e.g., 67 in FIG. 3A) fixedly attached to the driving shaft 60 for substantially limiting, in conjunction with at least one corresponding compression transmission surface a mating tool shaft 50,50', maximum axial movement of a mating tool shaft 50,50' with respect to the driving shaft 60 under an axial compression load. Compression transmission surface 67 in the illustrated embodiments of tool shaft coupler 15 has substantially the same shape and cross-sectional area as that portion of mating tool shaft 50,50' (i.e., compression transmission surface 55,55' respectively) illustrated in cross-section in FIG. 3C (i.e., substantially a semicircle having substantially one-half of the cross-sectional area of mating tool shaft 50,50' as illustrated). Note that compression transmission surface 67 may be reduced in size (e.g., by chamfering its edges) if the resulting area would substantially match or mate with the corresponding mating tool shaft compression transmission surface 55,55', and if the size reduction would not result in excessive material stress (i.e., leading to permanent deformation or premature failure) under the anticipated axial compression load.

The invention also comprises shaft locking means having an engagement surface 71 and being slidably coupled to the driving shaft 60 for reversibly locking said at least one tension-resisting member (i.e., balls 82,82') in a tension-resisting position. The shaft locking means in the illustrated embodiments comprises the spring stop ring 79, spring 78, spindle cap 70, and spindle cap nut 74, some interactions of which are described above. Note that the outer surface 73 of spindle cap 70 comprises a substantially frusto-conical surface 71 which in the illustrated embodiments functions as the engagement surface of the shaft locking means. Functions of the engagement surface 71 are described below.

In preferred embodiments, shaft locking means of the present invention may also comprise guide means for the shaft locking means. The guide means, in turn, may comprise one or more substantially longitudinal splines 87 on the stop ring 79 (which is then fixedly attached to driving shaft 60) matable with correspondingly spaced and numbered substantially longitudinal grooves 88 on the proximate surface of the shaft locking means (that is, on inner spindle cap surface 75 as schematically illustrated in FIGS. 1A and 1B). Alternative embodiments of the guide means (as in FIG. 4) may comprise one or more pairs of correspondingly spaced grooves or depressions 66,76 on proximate surfaces of the driving shaft 60 and/or spring stop ring 79 and the spindle cap 70 respectively, each pair of corresponding grooves or depressions 66,76 being coupled via one or more ball bearings 77 substantially free to roll and/or slide within the corresponding grooves or depressions 66,76 (but not outside of the grooves or depressions 66,76) when the shaft locking means is slidingly moved longitudinally with respect to the driving shaft 60. In either the spline/groove embodiment or the ball bearing/groove or depression embodiment, the shaft locking means will be substantially prevented by the guide means from rotating with respect to the driving shaft 60 about the rotational axis of the driving shaft (i.e., longitudinal axis BB), its preferred motion instead being a sliding motion in directions substantially parallel to the longitudinal axis BB.

Preferred embodiments of the invention may additionally comprise safety lock release means and attachment means 17. Attachment means 17 comprises at least one spindle cap access slot 32 (illustrated in two views in FIGS. 4 and 4A). Attachment means 17 may be reversibly coupled to the driving shaft housing end piece 65' (e.g., as by screw threads (as illustrated in FIGS. 1A and 1B), or a twist-lock connector which tends to be tightened when attachment means 17 is rotated in the expected direction of rotation of mating tool shaft 50,50') for guiding and supporting the mating tool shaft 50,50'.

Various sizes of attachment means 17 are illustrated in FIGS. 1A, 1B, 4, 4A and 5, each comprising a tubular attachment shaft 20, the proximal end of which may be reversibly secured within (e.g., as by set screw 35) or fixedly attached to attachment base 30. Within attachment shaft 20 are firmly but removably mounted at least one distal journal bearing 22 and at least one spacer tube 23. Note that journal bearing 22 (and, similarly, journal bearing 22'), as well as any other journal bearings of the present invention, each comprise one or more bearing elements, such as a ball bearing, a roller bearing or a sleeve bearing or some combination of such bearing elements. When a journal bearing comprises more than one bearing element, the adjacent bearing elements are preferably spaced apart distances less than or equal to the length of a single bearing element.

The journal bearing 22 is closely and slidably matable with a mating tool shaft 50,50', and the distal end of mating tool shaft 50,50' extends beyond the distal bearing 22 a second spacing distance when the tool shaft is drivingly coupled. The spacer tube acts to maintain a desired bearing mounting position as described below.

In the embodiment illustrated in FIG. 5, attachment means 17 comprises attachment shaft 20, two bearings 22,22' and two spacer tubes 23,23', both bearings 22,22' and both spacer tubes 23,23' being mounted substantially symmetrically about longitudinal axis BB within attachment shaft 20. Note that when attachment means 17 is coupled to driving shaft housing 65 (through driving shaft housing end piece 65') as in FIGS. 1A and 1B, a mating tool shaft 50,50' which is reversibly coupled to driving shaft 60 via coupler 15 will tend to be rotatable substantially about longitudinal axis BB. Any whipping tendency of mating tool shaft 50,50' will be at least substantially reduced by the guiding action of bearings 22,22' through which mating tool shaft 50,50' passes.

As noted above, certain embodiments of the tool shaft coupler 15 may have only one distal bearing 22 near the distal end of attachment shaft 20 (as when bearing 22' and its associated spacer tube 23' are not present). On the other hand, in embodiments of the tool shaft coupler 15 which comprise both bearings 22 and 22' and their associated spacer tubes 23 and 23' (as schematically illustrated in FIG. 5), then spacer tubes 23,23' and bearing 22' establish a first spacing distance between distal bearing 22 and the tension-resisting member(s) (e.g., balls 82,82'). Spacer tube 23 establishes a bearing-spacing distance between distal journal bearing 22 and proximal journal bearing 22'. When a mating tool shaft 50,50' is drivingly coupled to coupler 15, the distal end of tool shaft 50,50' extends distally to distal bearing 22 a second spacing distance.

In embodiments of tool shaft coupler 15 comprising proximal and distal bearings spaced as above, it has been empirically determined that vibration associated with high-speed rotation of a mating tool shaft 50,50' is minimized when the first spacing distance is greater than the second spacing distance and particularly when the second spacing distance approximately equals the bearing-spacing distance.

Substantially toroidal safety lock release means 18 are slidably positionable over said attachment means 17 and slidingly engagable through said at least one spindle cap access slot (e.g., access slots 32,32') with said engagement surface (e.g., see 71 on FIGS. 1A, 1B and 4) of said shaft locking means to move said shaft locking means to a first (unlocking) position (e.g., see the position of spindle cap 70 in FIG. 1A) for allowing said at least one tension-resisting member (e.g., see balls 82,82') to move from said tension-resisting position to allow reversible placement of a mating tool shaft 50,50' within said shaft locking means, and to allow movement of said shaft locking means to a second (locking) position (e.g., see the position of spindle cap 70 in FIG. 1B) for moving said at least one tension-resisting member (balls 82,82') to said tension-resisting position and for reversibly locking said at least one tension-resisting member (balls 82,82') in said tension-resisting position.

Toroidal safety lock release means 18 comprise at least one radially directed pin 42 (two substantially diametrically opposed pins 42,42' are illustrated in FIGS. 1A, 1B and 4) mounted fixedly in attachment ring 40 and extending far enough toward ring 40's longitudinal axis (e.g., see axis BB in FIGS. 1A, 1B and 4) to contact engagement surface 71 of spindle cap 70 through slot 32 in attachment means 17 (slots 32,32' are illustrated in FIGS. 1A, 1B and 4 to accept the two pins 42,42' which are also illustrated). Note that, because its larger diameter provides a convenient finger-gripping surface, toroidal safety lock release means 18 can be used to facilitate manually tightening or loosening attachment base 30 from its coupling (illustrated in FIGS. 1A and 1B as threaded) to driving shaft housing end piece 65'.

The tool shaft coupler shaft locking means engagement surface 71 may also interact with the safety lock release means to result in a driving shaft break-away torque of at least one inch-ounce with the safety lock release means in the first, unlocking, position. Note that engagement surface 71 and pins 42,42' may optionally be given complementarily formed or otherwise relatively high-friction surface finishes (e.g., as with matching machined grooves, knurling, sand-blasting or coating with frictional material). Sufficient friction force may then be developed between the pins 42,42' and engagement surface 71 to assure that sufficient braking force acts on spindle cap 70 (and thence through guide means to driving shaft 60) to exceed the break-away torque applied to driving shaft 60. This condition reversibly prevents rotation of driving shaft 60 with respect to driving shaft housing 65 when manual pressure is applied to attachment ring 40 to move (through pressure exerted by pins 42,42' on engagement surface 71) spindle cap 70 substantially into a first, unlocking, position. Note that for substantial (but still reversible) prevention of driving shaft 60 rotation with respect to driving shaft housing 65, complementary pin engagement means may optionally be employed. Complementary pin engagement means comprise at least one pin pair 91,92 fixedly coupled in opposing surfaces of spindle cap 70 and driving shaft housing end piece 65' as schematically illustrated in FIGS. 1A and 1B. Each pin pair 91,92 is sized and located so that the pins will overlap (see FIG. 1A) and thus mechanically (and reversibly) substantially prevent rotation of driving shaft 60 with respect to driving shaft housing end piece 65' (and thus with respect to driving shaft housing 65) when spindle cap 70 is in a first (unlocking) position. On the other hand, pin pair 91,92 is also sized so that the pins will not overlap (see FIG. 1B) and thus will not prevent rotation of driving shaft 60 with respect to driving shaft housing end piece 65' (and thus with respect to driving shaft housing 65) when spindle cap 70 is in a second (locking) position. For balance, preferred embodiments of the present invention which incorporate at least one pin pair 91,92 will preferably incorporate a plurality of such pin pairs spaced substantially equally around opposing surfaces of spindle cap 70 and driving shaft housing end piece 65'. When present, each pin pair 91,92 will preferably comprise ramp-like surfaces and be so spaced as to substantially prevent end-to-end interference between pins of a pin pair 91,92 when spindle cap 70 is being moved from a second (locking) position to a first (unlocking) position. In these latter embodiments, pin pairs 91,92 will still substantially (and reversibly) prevent rotation of driving shaft 60 with respect to driving shaft housing end piece 65' (and thus with respect to driving shaft housing 65) when spindle cap 70 is in a first (unlocking) position, but the pin pair(s) 91,92 will not substantially impede movement of spindle cap 70 into the first (unlocking) position.

Note also that attachment means 17 may additionally comprise in preferred embodiments warning means to visually indicate malfunction of said shaft locking means. Malfunction of the shaft locking means embodiments illustrated herein would result from a failure of spindle cap 70 to move from a first (unlocking) position to a second (locking) position under the influence of spring 78. Such failure to move even when no restraint is imposed through attachment ring 40 may be caused by a broken spring 78 and/or improper insertion of a mating tool shaft 50,50' through the tension transmission means resulting in a failure to effectively engage the mating tool shaft 50,50' with torque transmission surface 64. Failure to effectively engage torque transmission surface 64 will cause tension transmission surface 53,53' of the mating tool shaft 50,50' respectively to be positioned too far from a movable tension-resisting member (e.g., balls 82,82') to engage such member as attempts are made to move the member into an interference tension-resisting position. This is the condition illustrated schematically in FIG. 1A. Hence, with driving shaft 60 and mating tool shaft 50 in the relative positions illustrated in FIG. 1A, substantial release of manual pressure on attachment ring 40 will not result in spindle cap 70 moving to a second, locking, position where warning surface 99 would be substantially invisible (the condition illustrated in FIG. 1B). On the contrary, substantial release of manual pressure on attachment ring 40 under this condition will cause attachment ring 40 to remain in a position where warning surface 99 would remain substantially visible. Similar results would obtain in the case where attachment ring 40 was used to withdraw spindle cap 70 into a first, unlocking, position either after or simultaneous with breakage of spring 78.

Thus, warning means in preferred embodiments comprise at least a warning surface portion of said attachment means having a distinctive visual appearance (see, e.g., warning line 99 in FIGS. 4, 4A and 5), said warning portion being substantially visible with said toroidal safety lock release means contacting the shaft locking means in said first (unlocking) position, and said warning portion being substantially invisible with said toroidal safety lock release means contacting the shaft locking means in said second (locking) position. The desired distinctive visual appearance of the warning portion of the attachment means may be achieved, for example, with a contrasting surface finish or texture (e.g., knurled, matte or polished or machined grooves) and/or color (e.g., a yellow stripe on black) relative to adjacent attachment means surfaces.

The invention also comprises a mating tool shaft (e.g., 50,50') for coupling with a driving shaft 60 via a tool shaft coupler 15 as described herein, the mating tool shaft comprising at least one torque transmission surface 54,54', at least one tension transmission surface 53,53', and at least one compression transmission surface 55,55'. The torque transmission surface (e.g., 54' in FIG. 3A) is fixedly coupled to (or an integral part of) the mating tool shaft (e.g., 50' in FIG. 3A) for axially slidingly mating with said at least one torque transmission surface (e.g., 64 in FIG. 3A) of the tool shaft coupler 15 to transmit torque between the mating tool shaft 50,50' and the driving shaft 60.

At least one tension transmission surface (e.g., 53' in FIG. 3A) is spaced apart from said at least one torque transmission surface (e.g., 54 in FIG. 3A) to couple reversibly with said at least one movable tension-resisting member (e.g., balls 82,82') of the tool shaft coupler 15 to couple the driving shaft 60 and the mating tool shaft (e.g., 50' in FIG. 3A). Such coupling reversibly limits, in conjunction with at least one compression transmission surface fixedly coupled to (or an integral part of) the mating tool shaft and at least one compression transmission surface of the tool shaft coupler 15 (e.g., 55' and 67 respectively in FIG. 3A), maximum axial movement of the mating tool shaft with respect to the driving shaft under an axial load alternating between tension and compression.

Preferred embodiments of a mating tool shaft (e.g., 50' in FIG. 3A) comprise at least one tension transmission surface (e.g., 53' in FIG. 3A) spaced apart from one of said at least one compression transmission surface (e.g., 55' in FIG. 3A) about 0.223 inches (e.g., illustrated by the distance X' in FIG. 3A). In embodiments of the present invention using alternate compression transmission surface (e.g., 57' and 67' in FIG. 3A), a tension transmission surface such as 53' in FIG. 3A is preferably spaced apart from compression transmission surface 57' a distance X" which is less than the above spacing (of about 0.223 inches) but provides substantially the same limitation on maximum axial movement of the mating tool shaft (50' in FIG. 3A).

Figure 3C:
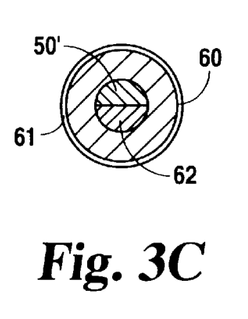
FIG. 3C schematically illustrates a cross section of a driving shaft and mating tool shaft effectively engaged as illustrated in FIG. 3B.

Note that a compression transmission surface of the present invention, whether coupled to driving shaft 60 or on a mating tool shaft, may have substantially the same shape as the portion of mating tool shaft 50' illustrated in cross-section in FIG. 3C, i.e., the cross-section may be substantially semicircular. In preferred embodiments of mating tool shafts 50,50', one or more warning bands 99' of distinctive visual appearance may be applied to the portion of a mating tool shaft surface adjacent to and just concealed by the attachment means 17 when the mating tool shaft is drivingly engaged with the tool shaft coupler 15 (as in FIG. 1B). Because such driving (effective) engagement implies sliding insertion of the mating tool shaft 50,50' within the coupler 15 to an effective depth wherein all corresponding axial force and torque transmission surfaces on the mating tool shaft and in the coupler are substantially fully engaged, faulty engagement of the force transmission surfaces occurs when the mating tool shaft is inserted in the coupler to a depth less than the effective depth. Insertion of a mating tool shaft 50,50' to a less-than-effective depth will then leave at least part of a visually distinctive portion 99' on the mating tool shaft unconcealed by the attachment means (as in FIG. 1A), thus providing a visual warning of the tool shaft's improper insertion into the coupler 15.

Figure 2:
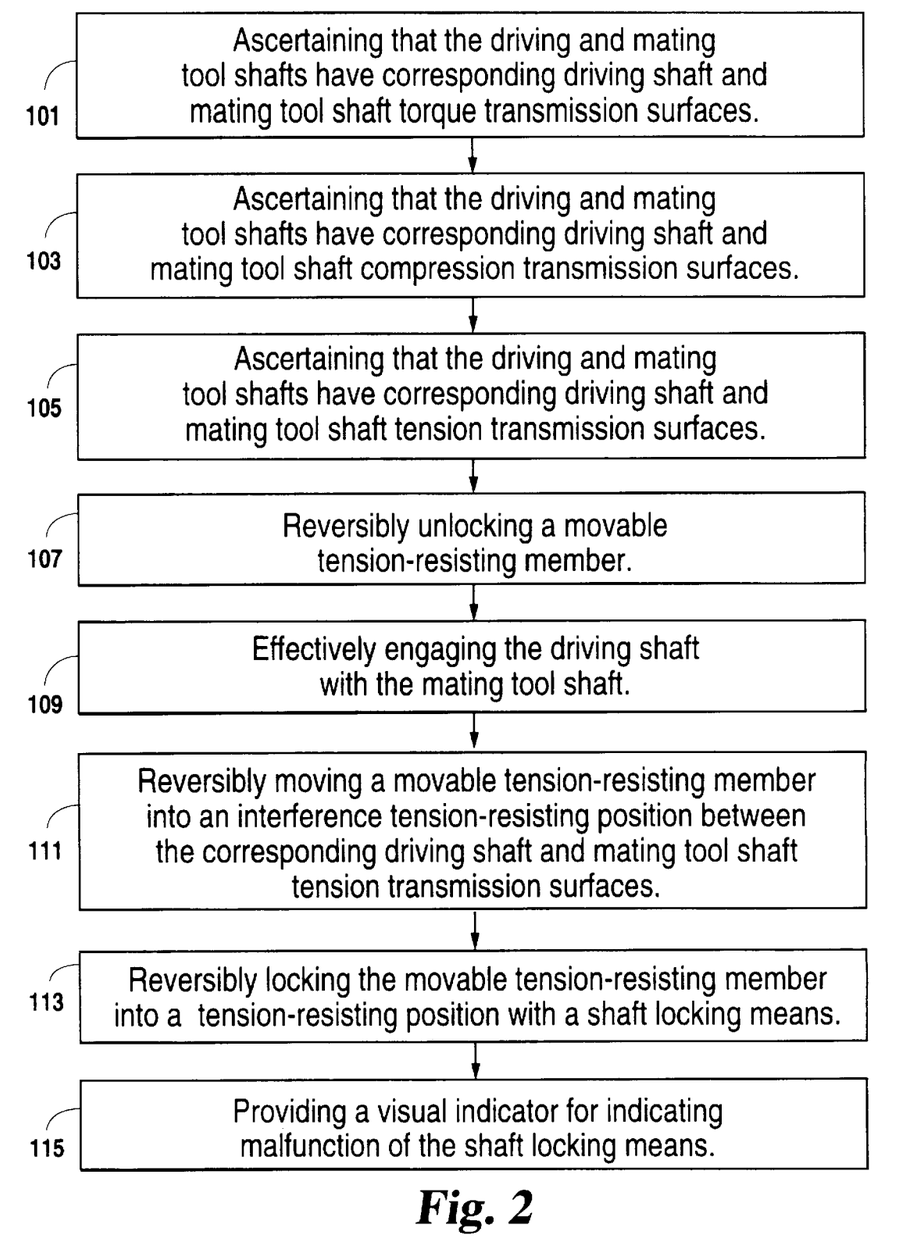
FIG. 2 schematically illustrates the steps of a method of reversibly coupling a driving shaft and a mating tool shaft.

The present invention also comprises a method (schematically illustrated as a flow chart in FIG. 2) of reversibly coupling a driving shaft and a mating tool shaft, the method comprising (step 101) ascertaining that the driving and mating tool shafts have corresponding driving shaft and mating tool shaft torque transmission surfaces drivingly attached to (or an integral part of) the driving and mating tool shafts respectively to transmit torque between the driving and mating tool shafts; (step 103) ascertaining that the driving and mating tool shafts have corresponding driving shaft and mating tool shaft compression transmission surfaces drivingly attached to (or an integral part of) the driving and mating tool shafts respectively to transmit axial compressive forces between the driving and mating tool shafts; (step 105) ascertaining that the driving and mating tool shafts have corresponding driving shaft and mating tool shaft tension transmission surfaces drivingly attached to (or an integral part of) the driving and mating tool shafts respectively to transmit axial tension forces between the driving and mating tool shafts, said driving shaft tension transmission surface being spaced apart from said driving shaft torque transmission surface, and said mating tool shaft tension transmission surface being spaced apart from said mating tool shaft torque transmission surface; (step 107) reversibly unlocking a movable tension-resisting member, allowing movement of said member out of a tension-resisting position between said corresponding driving shaft and mating tool shaft tension transmission surfaces; (step 109) effectively engaging the driving shaft with the mating tool shaft so that respective corresponding portions of torque transmission surfaces, tension transmission surfaces, and compression transmission surfaces of the driving and mating tool shafts are proximate; (step 111) reversibly moving a movable tension-resisting member into a tension-resisting position between said corresponding driving shaft and mating tool shaft tension transmission surfaces for transmitting axial tension force between said driving shaft and said mating tool shaft by compression of said tension-resisting member; (step 113) reversibly locking said movable tension-resisting member into said tension-resisting position with a shaft locking means; and (step 115) providing a visual indicator for indicating malfunction of the shaft locking means as described herein.

What is claimed is:

1. A tool shaft coupler for drivingly coupling a driving shaft with a mating tool shaft which has proximal and distal ends and which is effectively engaged with the driving shaft, the driving shaft being rotatable about a substantially longitudinal axis within a driving shaft housing, the coupler comprising:

at least one torque transmission surface fixedly coupled to the driving shaft for axially slidingly mating with a mating tool shaft to transmit torque between the mating tool shaft and the driving shaft;

tension transmission means spaced apart from said at least one torque transmission surface and comprising at least one tension transmission surface and at least one movable tension-resisting member, said at least one tension-resisting member being reversibly and slidingly movable to a tension-resisting position to couple the driving shaft and a mating tool shaft to reversibly limit maximum axial movement of the mating tool shaft with respect to the driving shaft under an axial tension load;

at least one compression transmission surface fixedly coupled to the driving shaft for substantially limiting maximum axial movement of a mating tool shaft with respect to the driving shaft under an axial compression load;

shaft locking means having an engagement surface and being slidably coupled to the driving shaft for reversibly locking said at least one tension-resisting member in a tension-resisting position;

attachment means reversibly coupled to the driving shaft housing for guiding and supporting the mating tool shaft, said attachment means comprising at least one spindle cap access slot; and substantially toroidal safety lock release means slidably positionable over said attachment means and slidingly engagable through said at least one spindle cap access slot with said engagement surface of said shaft locking means to move said shaft locking means to a first unlocking position for allowing said at least one tension-resisting member to move from said tension-resisting position to allow reversible placement of a mating tool shaft within said shaft locking means, and to allow movement of said shaft locking means to a second locking position for moving said at least one tension-resisting member to said tension-resisting position and for locking said at least one tension-resisting member in said tension-resisting position.

2. The tool shaft coupler of claim 1 additionally comprising warning means to visually indicate malfunction of said shaft locking means.

3. The tool shaft coupler of claim 1 wherein said substantially toroidal safety lock release means comprises two radially directed pins.

4. The tool shaft coupler of claim 3 wherein said attachment means comprises two spindle cap access slots.

5. The tool shaft coupler of claim 4 wherein said warning means comprise at least a warning portion of said attachment means having a distinctive visual appearance, said warning portion being substantially visible with said toroidal safety lock release means contacting said shaft locking means in said first unlocking position, and said warning portion being substantially invisible with said toroidal safety lock release means contacting said shaft locking means in said second locking position.

6. The tool shaft coupler of claim 5 wherein said shaft locking means engagement surface interacting with said safety lock release means results in a driving shaft breakaway torque of at least one inch-ounce with said safety lock release means in said first unlocking position.

7. The tool shaft coupler of claim 6 wherein said at least one torque transmission surface lies substantially in a single plane.

8. The tool shaft coupler of claim 7 wherein said at least one movable tension-resisting member comprises three balls.

9. The tool shaft coupler of claim 8 wherein said balls comprise chrome steel.

10. The tool shaft coupler of claim 1 wherein said attachment means additionally comprises a distal tool shaft bearing spaced apart from said at least one tension-resisting member by a first spacing distance and from the distal end of a drivingly coupled tool shaft by a second spacing distance, said first spacing distance being greater than said second spacing distance.

11. The tool shaft coupler of claim 10 wherein said attachment means additionally comprises a proximal tool shaft bearing spaced apart from said distal tool shaft bearing a bearing-spacing distance.

12. The tool shaft coupler of claim 11 wherein said bearing-spacing distance approximately equals said second spacing distance.

13. The tool shaft coupler of claim 11 wherein said tension-resisting member, when not contacting a mating tool shaft tension transmission surface, can not simultaneously contact said shaft locking means and a mating tool shaft.

14. The tool shaft coupler of claim 11 wherein said tension-resisting member can not contact a mating tool shaft except at a tension transmission surface.

15. A tool shaft coupler for drivingly coupling a driving shaft with a mating tool shaft, the driving shaft being rotatable about a substantially longitudinal axis within a driving shaft housing, the coupler comprising:

at least one torque transmission surface fixedly coupled to the driving shaft for axially slidingly mating with a mating tool shaft;

tension transmission means spaced apart from said at least one torque transmission surface and comprising at least one tension transmission surface and at least one moveable tension-resisting member, said at least one tension-resisting member being reversibly and slidingly moveable to a tension-resisting position;

at least one compression transmission surface fixedly coupled to the driving shaft;

shaft locking means having an engagement surface and being slidably coupled to the driving shaft for reversibly locking said at least one tension-resisting member in a tension-resisting position; and attachment means reversibly coupled to the driving shaft housing for guiding said shaft locking means, said attachment means comprising at least one slot for accessing said shaft locking means.

16. The tool shaft coupler of claim 15 wherein said shaft locking means and the driving shaft housing comprise complementary pin engagement means.

17. The tool shaft coupler of claim 15 additionally comprising safety lock release means slidingly engaged around said attachment means, said safety lock release means having at least one elongated member which engages said engagement surface of said shaft locking means through said access slot of said attachment means for moving said shaft locking means between a first locking position and a second unlocking position.

18. The tool shaft coupler of claim 15 wherein said attachment means comprises at least one substantially cylindrical member.

19. The tool shaft coupler of claim 15 additionally comprising warning means to visually indicate malfunction of said shaft locking means.

20. A tool shaft coupler for drivingly coupling a driving shaft with a mating tool shaft, the driving shaft being rotatable about a substantially longitudinal axis within a driving shaft housing, the coupler comprising:

at least one torque transmission surface fixedly coupled to the driving shaft and axially slidingly matable with a mating tool shaft;

tension transmission means spaced apart from said at least one torque transmission surface and comprising at least one tension transmission surface and at least one moveable tension-resisting member, said at least one tension-resisting member being reversibly and slidingly moveable to a tension-resisting position;

at least one compression transmission surface fixedly coupled to the driving shaft;

a first substantially cylindrical member slidably coupled to the driving shaft, said first substantially cylindrical member having an inner cam surface for moving said tension transmission means into the tension-resisting position and an outer surface configured for engagement;

a tubular member connected to the housing, said tubular member comprising at least one longitudinal slot and substantially enclosing said first substantially cylindrical member; and a second substantially cylindrical member operatively connected to said outer surface of said first substantially cylindrical member through said at least one longitudinal slot.

21. The tool shaft coupler of claim 20, additionally comprising warning means to visually indicate malfunction of said coupler.

22. The tool shaft coupler of claim 20 wherein said tubular member comprises at least two slots.

23. A tool shaft coupler for drivingly coupling a driving shaft with a mating tool shaft, the driving shaft being rotatable about a substantially longitudinal axis within a driving shaft housing, said coupler comprising:

at least one torque transmission surface coupled to or integral with the driving shaft and axially slidingly matable with the mating tool shaft;

at least one tension transmission surface coupled to or integral with the driving shaft;

at least one tension-resisting member, said member being reversibly and slidingly moveable to a tension-resisting position in which said at least one tension-resisting member is proximate to said at least one tension transmission surface;

at least one compression transmission surface coupled to or integral with the driving shaft;

a first substantially cylindrical member slidably coupled to the driving shaft, said first substantially cylindrical member having an inner cam surface for moving said at least one tension-resisting member into the tension resisting position and an outer surface configured for engagement;

a tubular member connected to the housing, said tubular member comprising at least one longitudinal slot and substantially enclosing said first substantially cylindrical member; and a second substantially cylindrical member operatively connected to said outer surface of said first substantially cylindrical member through said at least one longitudinal slot.

24. A mating tool shaft comprising:

at least one torque transmission surface configured to axially slidingly engage with substantially the entire torque transmission surface of the coupler of claim 15;

at least one tension transmission surface, spaced apart from said at least one torque transmission surface of said shaft, wherein said at least one tension transmission surface is configured to abut the at least one tension-resisting member of the coupler of claim 15; and at least one compression transmission surface, wherein said at least one compression transmission surface is configured to abut the at least one compression transmission surface of the coupler of claim 15.

25. The mating tool shaft of claim 24 wherein said shaft is substantially cylindrical.

26. The mating tool shaft of claim 24, wherein said at least one tension transmission surface comprises a wall bounding an annular groove around said shaft.

27. The mating tool shaft of claim 26 wherein said shaft, when operationally engaged, contacts said tension-resisting member, if at all, along said wall.

28. A mating tool shaft for reducing tool shaft vibration, comprising:

a sectioned proximal end having at least one surface corresponding to the at least one torque transmission surface of the coupler of claim 15, and at least one compression transmission surface corresponding to the at least one compression transmission surface of the coupler of claim 15;

a medial portion having an annular groove spaced apart from said sectioned proximal end, said annular groove bounded by at least one tension transmission surface corresponding to the tension transmission means of the coupler of claim 15; and wherein said tool shaft contacts said tension transmission means, if at all, only on said tension transmission surface.

29. The mating tool shaft of claim 28 wherein said annular groove is spaced apart from said sectioned proximal end by about 0.223 inches.

30. The mating tool shaft of claim 28 wherein at least one of said at least one tension transmission surfaces of said shaft is substantially frusto-conical.

31. The mating tool shaft of claim 28, wherein said proximal end is substantially half-cylindrical.

32. A mating tool shaft having a longitudinal axis for use with a tool shaft coupler having at least one torque transmission surface, at least one compression transmission surface, at least one tension transmission surface, at least one tension-resisting member, shaft locking means and attachment means, said mating tool shaft comprising:

a proximal end having at least one surface configured to engage with the torque transmission surface of the tool shaft coupler and at least one surface configured to engage with the compression transmission surface of the tool shaft coupler under a compression load; and a medial portion having an annular groove spaced apart from said proximal end, said annular groove being bounded by at least one surface and being configured so that only said at least one surface bounding said groove contacts the at least one tension-resisting member.

33. The mating tool shaft of claim 32 wherein said surfaces of said proximal end form a cross-section of said shaft.

34. The mating tool shaft of claim 33 wherein said at least one surface of said proximal end configured to engage with the torque transmission surface is parallel to the longitudinal axis of said shaft and said at least one surface of said proximal end configured to engage with the compression transmission surface is perpendicular to the longitudinal axis of said shaft.

35. The mating tool shaft of claim 33 wherein said at least one surface bounding said groove is spaced apart from said at least one surface configured to engage with the compression transmission surface of said proximal end by about 0.223 inches.

36. The mating tool shaft of claim 35 wherein one of said at least one compression transmission surfaces is substantially semicircular.

37. The mating tool shaft of claim 32, wherein said proximal end has only one surface configured to engage with the torque transmission surface of the tool shaft coupler.

38. The mating tool shaft of claim 32, wherein said proximal end has only one secondary surface adjoining said at least one surface configured to engage with the torque transmission surface of the tool shaft coupler, said secondary surface forming a portion of a cylinder.

39. The mating tool shaft of claim 32 additionally comprising a visually distinct proximal portion which is visible when said mating tool shaft is not drivingly coupled to said tool shaft coupler, but which is not visible outside of said attachment means when said mating tool shaft is drivingly coupled to said tool shaft coupler.

\* \* \* \* \*